United States Patent
Warthoe (10) Patent No.: US 8,153,780 B2
(45) Date of Patent: Apr. 10, 2012

(54) REPORTER UNIT FOR DETECTION OF TARGET MOLECULES USING POLYMERISABLE SUBSTRATE

(75) Inventor: Peter Warthoe, Copenhagen Ø (DK)

(73) Assignee: Atonomics A/S, Copenhagen (DK)

( * ) Notice: Subject to any disclaimer, the term of this patent is extended or adjusted under 35 U.S.C. 154(b) by 345 days.

(21) Appl. No.: 12/449,357

(22) PCT Filed: Feb. 6, 2008

(86) PCT No.: PCT/DK2008/000053
§ 371 (c)(1),
(2), (4) Date: Aug. 4, 2009

(87) PCT Pub. No.: WO2008/095493
PCT Pub. Date: Aug. 14, 2008

(65) Prior Publication Data
US 2010/0099089 A1    Apr. 22, 2010

Related U.S. Application Data

(60) Provisional application No. 60/890,411, filed on Feb. 16, 2007.

(30) Foreign Application Priority Data

Feb. 6, 2007    (DK) .................................. 2007 00205

(51) Int. Cl.
*C07H 19/04*    (2006.01)
*C12Q 1/68*    (2006.01)
*C12P 19/34*    (2006.01)

(52) U.S. Cl. .................. 536/26.6; 435/6.1; 435/91.1
(58) Field of Classification Search .................. 536/26.6; 435/6.1, 91.1
See application file for complete search history.

(56) References Cited

U.S. PATENT DOCUMENTS
4,749,647 A    6/1988  Thomas et al.
5,807,942 A    9/1998  Sakaki et al.

FOREIGN PATENT DOCUMENTS
EP    1 343 012 A1    9/2003
WO    00/32813 A1    6/2000

OTHER PUBLICATIONS

Liu, H., et al. "TaqMan probe array for quantitative detection of DNA targets"; Nucleic Acids Research; 2006; vol. 34; No. 1; pp. 1-8; Oxford University Press; XP-002474945.

Gao, Z., et al. "Detection of nucleic acids using enzyme-catalyzed template-guided deposition of polyaniline"; Advanced Materials; 2007; vol. 19; pp. 602-606; WILEY-VCH Verlag GmbH & Co., KGaA, Weinheim; XP-002474944.

*Primary Examiner* — Jezia Riley
(74) *Attorney, Agent, or Firm* — The Nath Law Group; Joshua B. Goldberg; Tanya E. Harkins (57) ABSTRACT

The invention relates to a reporter unit for detecting a target molecule comprising at least one component attached to a target molecule specific probe, wherein said at least one component is liberated from said probe by the activity of a first enzyme thereby making the at least one component available as a substrate for a second enzyme which employs the substrate in a polymerization reaction to obtain a detectable structure.

20 Claims, 4 Drawing Sheets

Step 1.

Step 2.

Step 3.

SAW Sensor
↓
Frequency Response

REPORTER UNIT FOR DETECTION OF TARGET MOLECULES USING POLYMERISABLE SUBSTRATE

This is a National Phase Application filed under 35 U.S.C. 371 as a national stage of PCT/DK2008/000053, filed on Feb. 6, 2008, an application claiming the benefit of Danish Patent Application PA 2007 00205, filed on Feb. 6, 2007, and claiming the benefit under 35 USC 119(e) of U.S. Provisional Application No. 60/890,411, filed on Feb. 16, 2007, the entire content of each of which is hereby incorporated by reference in its entirety.

TECHNICAL FIELD

The invention relates to the field of detecting target molecules. In particular, the invention pertains to a novel reporter unit and novel reporter unit system and their use which provides for the detection of target molecules of both protein and nucleic acid origin.

BACKGROUND

Sensitive detection systems that are able to register the presence of very small target molecules and their interaction with other molecules are currently based on detection systems employing reagents such as dyes, fluorophores with or without quenchers, radioactive substances, etc. Most systems known in the art require the design of a fluorescent labelled hybridization probe which only emits a signal upon binding to its target nucleic acid. The following examples of various detection systems in the field of molecular biology are all well known and commonly used in the art:

The DNA binding dye technique utilizes that the amount of double stranded amplification product usually exceeds the amount of nucleic acid originally present in the sample to be analyzed. Double-stranded DNA specific dyes may be used, which upon excitation with an appropriate wavelength show enhanced fluorescence only if they are bound to double-stranded DNA. Preferably, only those dyes may be used which like SybrGreenl I, for example, do not affect the efficiency of the polymerase chain reaction (PCR).

The TaqMan probe is a single-stranded hybridization probe labelled with two components. When the first component is excited with light of a suitable wavelength, the absorbed energy is transferred to the second component, the so-called quencher, according to the principle of fluorescence resonance energy transfer. During the annealing step of the PCR reaction, the hybridization probe binds to the target DNA and is degraded by the 5' exonuclease activity of the Taq polymerase during the subsequent elongation phase. As a result the excited fluorescent component and the quencher are spatially separated from one another and thus a fluorescence emission of the first component can be measured.

The Molecular Beacon is a hybridization probe that is also labelled with two components, a label and a quencher, the components preferably being located at each ends of the probe. As a result of the secondary structure of the probe, both components are in spatial vicinity in solution. After hybridization to the target nucleic acids both components are separated from one another such that after excitation with light of a suitable wavelength the fluorescence emission of the first component can be measured.

Single Label Probe (SLP) detection consists of a single oligonucleotide labelled with a single fluorescent dye at either the 5'- or 3'-end. Two different designs can be used for oligo labelling: G-Quenching Probes and Nitroindole-De-quenching probes. In the GQuenching embodiment, the fluorescent dye is attached to a C at oligo 5'- or 3'-end. Fluorescence decreases significantly when the probe is hybridized to the target, in case two G's are located on the target strand opposite to C and in position 1 aside of complementary oligonucleotide probe. In the Nitroindole Dequenching embodiment, the fluorescent dye is attached to Nitroindole at the 5'- or 3'-end of the oligonucleotide. Nitroindole somehow decreases the fluorescent signaling of the free probe. Fluorescence increases when the probe is hybridized to the target DNA due to a dequenching effect.

The FRET hybridization probe is especially useful for all kinds of homogenous hybridization assays. It is characterized by a pair of two single-stranded hybridization probes which are used simultaneously and are complementary to adjacent sites of the same strand of the amplified target nucleic acid. Both probes are labelled with different fluorescent components. When excited with light of a suitable wavelength, a first component transfers the absorbed energy to the second component according to the principle of fluorescence resonance energy transfer such that a fluorescence emission of the second component can be measured when both hybridization probes bind to adjacent positions of the target molecule to be detected. When annealed to the target sequence, the hybridization probes must sit very close to each other, in a head to tail arrangement. Usually, the gap between the labelled 3' end of the first probe and the labelled 5' end or the second probe is as small as possible, i.e. 1-5 bases. This allows for a close vicinity of the FRET donor compound and the FRET acceptor compound, which is typically 10-100 Angstroem.

In addition to and as an alternative it would be desirable to obtain a sensitive detection system devoid of the requirement for the currently used labels such as e.g. dyes, fluorophores with and without quenchers, radioactive substances, etc.

DISCLOSURE OF THE INVENTION

In a first aspect the invention relates to a reporter unit for detecting a target molecule comprising at least one component attached to a target molecule specific probe, wherein said at least one component is liberated from said probe by the activity of a first enzyme thereby making the at least one component available as a substrate for a second enzyme which employs the substrate in a polymerization reaction to obtain a detectable structure.

In a second aspect the invention relates to a reporter unit system for detecting a target molecule comprising a target molecule specific probe attached to a first enzyme, said first enzyme is cleaving a pre-substrate comprising at least one component thereby liberating the at least one component as a substrate for a second enzyme which employs the substrate in a polymerization reaction to obtain a detectable structure.

In a third aspect the invention relates to a reporter unit system for detecting a target molecule comprising one component and a target molecule specific probe attached to a second enzyme, said second enzyme employing the one component as a substrate in a polymerization reaction to obtain a detectable structure.

In a fourth aspect the invention relates to the use of the reporter unit for detecting a target molecule comprising the steps: a) Adding the reporter unit to a test sample potentially comprising the target molecule; b) Exposing the reporter unit/sample mixture of a) to the first enzyme; c) Exposing the mixture of b) to the second enzyme; and d) Detecting the polymerized structure.

In a fifth aspect the invention relates to the use of the reporter unit for detecting a nucleic acid target molecule comprising the steps: a) Adding the reporter unit to a test sample potentially comprising the target molecule; b) Exposing the reporter unit/sample mixture of a) to the first enzyme, wherein said first enzyme has double stranded exonuclease activity; c) Exposing the mixture of b) to the second enzyme; and d) Analysing the polymerized structure on a SAW sensor.

In a sixth aspect the invention relates to the use of the reporter unit for detecting a protein target molecule comprising the steps: a) Adding the reporter unit to the test sample potentially comprising the target molecule; b) Exposing the reporter unit/sample mixture of a) to the first enzyme, wherein said first enzyme has single stranded exonuclease activity; c) Exposing the mixture of b) to the second enzyme; and d) Analysing the polymerized structure on a SAW sensor.

In a seventh aspect the invention relates to the use of the reporter unit system for detecting a protein target molecule comprising the steps: a) Adding the test sample potentially comprising the target molecule to a target molecule specific immobilising agent; b) Adding the first enzyme linked to a target molecule specific probe to the mixture of a); c) Adding the pre-substrate comprising at least one component to the mixture of b); d) Adding the second enzyme to the mixture of c); and e) Analysing the polymerized structure on a SAW sensor.

In a eighth aspect the invention relates to the use of the reporter unit system for detecting a protein target molecule comprising the steps: a) Adding the test sample potentially comprising the target molecule to a target molecule specific immobilising agent; b) Adding the second enzyme linked to a target molecule specific probe to the mixture of a); c) Adding the substrate to the mixture of b); and d) Analysing the polymerized structure on a SAW sensor.

BRIEF DESCRIPTION OF THE DRAWINGS

The invention is explained in detail below with reference to the drawing(s), in which FIG. 1 illustrates a method for detecting a target molecule on the SAW sensor surface (13) of a micro sensor. The recognition unit of the invention (4) is used to monitor the presence of a target molecule (1). In certain embodiments the invention relates to a method further comprising a step of nucleic acid amplification of the target molecule (step 1) employing a nucleic acid polymerase having 5'-3' nuclease activity (a first enzyme), a set of forward (2) and reverse (3) primers capable of hybridizing to the target sequence and the recognition unit of the invention (4) which is capable of hybridizing to the target sequence 3' relative to the forward primer (2). The nucleic acid polymerase digests the recognition unit of the invention (4) during amplification (step 2) when it is hybridized to the target sequence, thereby liberating the substrate (6) from the digested nucleotides (5). The liberated substrate, 3HB-CoA (6) is employed by the PHA synthase (9,10) to form larges PHA molecules (11, 12) by the polymerization reaction (step 3). The polymerised structures are directly detectable by a mass induced frequency change on the SAW sensor surface.

FIG. 2 illustrates a method for measuring a protein or peptide target molecule in a test sample on a SAW sensor surface (1) of a micro sensor. In step 1 is the first antibody (4) attached to the walls of the SAW sensor cavity. The analyte (5) is interacting with the first (4) and the second antibody (6) the latter having a second enzyme (7) attached. On the SAW sensor surface are immobilized an enzyme (2) capable of polymerizing the substrate to generate polymers. An pre-substrate are injected into the SAW cavity (8,9). In step 2 are the second enzyme (7) cleaving the pre-substrate (8,9) thereby releasing the substrate (10). In step 3 is the released substrate interacting with the immobilized enzyme on the SAW sensor surface generating polymer structures that is detected by the SAW sensor due to mass increase on the SAW sensor surface. 1; The SAW sensor surface, 2; The immobilized enzyme (PHA Synthase), 3; The wall of the SAW cavity, 4; The catching antibody, 5; The analyte, 6; The secondary antibody having an second enzyme attached (7), 8+9; The pre-substrate for the PHA synthase (2), 10; The release substrate, 12; The released substrate attaching to the immobilized PHA Synthase, 13,14 and 15; The ongoing polymerization process.

DETAILED DESCRIPTION OF THE INVENTION

In one embodiment the invention relates to a reporter unit for detecting a target molecule comprising at least one component attached to a target molecule specific probe, wherein said at least one component is liberated from said probe by the activity of a first enzyme thereby making the at least one component available as a substrate for a second enzyme which employs the substrate in a polymerization reaction to obtain a detectable structure.

In one embodiment the invention relates to a reporter unit system for detecting a target molecule comprising a target molecule specific probe attached to a first enzyme, said first enzyme is cleaving a pre-substrate comprising at least one component thereby liberating the at least one component as a substrate for a second enzyme which employs the substrate in a polymerization reaction to obtain a detectable structure.

In one embodiment the invention relates to a reporter unit system for detecting a target molecule comprising a substrate and a target molecule specific probe attached to a second enzyme, said second enzyme employs the substrate in a polymerization reaction to obtain a detectable structure.

In one embodiment the invention relates to a reporter unit. or reporter unit system, wherein the at least one component is a coenzyme A (CoA) ester selected from the group consisting of: (R)-3-Hydroxyacyl-CoA, (R)-3-Hydroxypropyryl-CoA, (R)-3-Hydroxybutyryl-CoA and Lactoyl-CoA, or (R)-3-Hydroxybutyryl-N-acetylcysteamin, where R is H, CH3, C2H5, C3H7, C4H9, C5H11, C6H13, C7H15, C8H17, C9H19, COH21, C11H23, C12H25, C13H27 or C14H29.

Polyhydroxyalkanoates (PHA) are linear polymer belonging to the polyesters class, and which polyoxoesters are produced in nature by a wide range of bacteria as energy storage compounds. The polymer is primarily a product of carbon assimilation from glucose or starch and is employed by micro-organisms as a form of energy storage molecule to be metabolized when other common energy sources are not available. More than 100 different monomer substrates can be combined within this family to give materials with extremely different properties. They can be either thermoplasic or elastomeric materials, with melting points ranging from 40 to 180° C., making them useful for the production of bulk and specialty plastics. PHA is also biodegradable and current interest in PHA stems from its potential applications within the emerging field of biopolymer engineering, a major new application for recombinant DNA technology. Furthermore, the mechanical properties and characteristics, and the biocompatibility of PHA can be changed by blending, modifying the surface or combining PHA with other polymers, enzymes and inorganic materials, making it possible for a wider range of applications.

The most common type of PHA is polyhydroxybutyrate (PHB). Microbial biosynthesis of PHB starts with the condensation of two molecules of acetyl-CoA to give acetoacetyl-CoA which is subsequently reduced to hydroxybutyryl-CoA. This latter compound is then used as a monomer substrate to polymerize PHB. PHB has attracted much commercial interest as a plastic material because its physical properties are remarkably similar to those of polypropylene (PP), even though the two polymers have quite different chemical structures. While PHB appears stiff and brittle, it also exhibits a high degree of crystallinity, a high melting point of about 180° C., but, most importantly, PHB is rapidly biodegradable, unlike PP. The poly-3-hydroxybutyrate (P3HB) form of PHB is probably the most common type of polyhydroxyalkanoate, but many other polymers of this class are produced by a variety of organisms, such as e.g. poly-4-hydroxybutyrate (P4HB), polyhydroxyvalerate (PHV), polyhydroxyhexanoate (PHH), polyhydroxyoctanoate (PHO) and their copolymers. The PHB copolymer polyhydroxybutyrate-valerate (PHBV) is less stiff and tougher than PHB.

Structure of PHA.

PHA

Short chain length
R = H, CH$_3$, CH$_2$CH$_3$
Medium chain length
R = (CH$_2$)$_2$CH$_3$ to (CH$_2$)$_8$CH$_3$ Structure of P3HB, PHV and their copolymer PHBV.

-continued

PHV

In one embodiment the invention relates to a reporter unit or reporter unit system, wherein the at least one component furthermore is attached to a label selected from the group consisting of: dyes, fluorophores, quenchers, and radioactive substances.

In one embodiment the invention relates to a reporter unit or reporter unit system, wherein the probe comprises nucleic acids, nucleic acid derivatives, nucleic acid analogues, proteins, protein derivatives, protein analogues or any combination thereof.

In one embodiment the invention relates to a reporter unit, wherein the at least one component is attached to the probe at the 3'terminus or the 5'terminus or both at the 3'terminus and the 5'terminus.

In one embodiment the invention relates to a reporter unit, wherein the probe comprises proteins, protein derivatives, protein analogues and wherein the at least one component is attached to the probe at the amino terminus or the carboxy terminus or both at the amino terminus and the carboxy terminus.

In one embodiment the invention relates to a reporter unit or reporter unit system, wherein the probe comprises a blocking component at the 3'terminus whereby the probe is not able to extend the DNA strand from the 3'end.

The oligonucleotide probe is constructed in such a way that it exists in at least one single-stranded conformation when unhybridized and one double stranded conformation when hybridized to a target polynucleotide.

In one embodiment the invention relates to a reporter unit or reporter unit system, wherein the first enzyme has double stranded exonuclease activity.

In one embodiment the invention relates to a reporter unit or reporter unit system, wherein the first enzyme is taq polymerase.

In one embodiment the invention relates to a reporter unit or reporter unit system, wherein the first enzyme has single stranded exonuclease activity.

In one embodiment the Invention relates to a reporter unit or reporter unit system, wherein the first enzyme is Exo I.

In one embodiment the invention relates to a reporter unit or reporter unit system, wherein the first enzyme has 5' terminus exonuclease activity.

In one embodiment the invention relates to a reporter unit or reporter unit system, wherein the second enzyme is selected from the group consisting of: Polyhydroxyalkanoate (PHA) synthases and polyhydroxybutyrate (PHB) synthases.

"PHA synthase" as used herein, also means PHA polymerase and phaC. PHA synthases play a central catalytic role in PHA synthesis and granule formation by catalyzing the polymerization of hydroxyacyl-CoA substrates to yield PHA, which in turn associate to form PHA granules. A cysteine residue conserved among all known PHA synthases is involved in the covalent catalysis. The synthases share structural and functional similarities with lipases. PHA synthase can, in addition to the normal substrate R-3-hydroxybutyryl-CoA, recognize two substrate analogs, lactoyl-CoA and R-3-hydroxybutyryl-N-acetylcysteamine.

In one embodiment the Invention relates to a reporter unit or reporter unit system, wherein the Polyhydroxyalkanoate (PHA) synthase is a class I, class II, class III or class IV synthase. There are four classes (I-IV) of PHA synthases based on their nucleotide and predicted amino acid sequences. These classes have different substrate specificity and are involved in generation of different polymers.

In one embodiment the Invention relates to a reporter unit or reporter unit system, wherein the first enzyme and/or the second enzyme is thermostable.

Thermostability is in particular useful when the reporter unit or reporter unit system furthermore is applied in combination with polymerase chain reaction (PCR).

In one embodiment the invention relates to a reporter unit or reporter unit system, wherein the polymerized structure is detected by monitoring polymer related changes in mass, optical density, viscosity, label or any combination thereof.

In some embodiments the polymerization reaction results in a polymerized structure that may be directly detected by a frequency change due to a mass increase on the surface of a SAW sensor.

In some embodiments the polymerized structure may also be detected by fluorescence using dye molecules such as Nile red. The oxazine dye Nile blue A and its fluorescent oxazone form, Nile red, binds strongly to polyhydroxyalkanoic acids (PHA).

In some embodiments, the formation of the polymerized structure may be detected directly by measuring the optical density at certain wavelength such as e.g. 600 nm during the polymerization reaction.

In some embodiments the polymerised structure may be detected directly by monitoring the release of CoA-SH during the polymerization reaction.

Further according to the invention the release of substrate (3HB-CoA) can be used as a positive feed back switch using CoA-SH and HSOCCH2CHOHCH3 as substrate for the PHA synthase.

In one embodiment the invention relates to a use of the reporter unit for detecting a target molecule comprising the steps: a) Adding the reporter unit to a test sample potentially comprising the target molecule; b) Exposing the reporter unit/sample mixture of a) to the first enzyme; c) Exposing the mixture of b) to the second enzyme; and d) Detecting the polymerized structure.

In one embodiment the invention relates to a use of the reporter unit for detecting a nucleic acid target molecule comprising the steps: a) Adding the reporter unit to a test sample potentially comprising the target molecule; b) Exposing the reporter unit/sample mixture of a) to the first enzyme, wherein said first enzyme has double stranded exonuclease activity; c) Exposing the mixture of b) to the second enzyme; and d) Analysing the polymerized structure on a SAW sensor.

The invention particular relates to a method designing the real time PCR technology so a SAW resonator microsensor can applied as a real time detector unit instead of fluorescence based real time PCR assays.

Surface acoustic wave (SAW) technology is known as a very sensitive system employed in detecting amounts of target molecules in the nano-micro range. It is based on the detection of target molecule associated changes in mass and structure which affect the transmission of waves through the SAW sensor substrate. However, certain target molecule interactions does not provide for changes that are large enough to be detected directly by SAW technology, such as e.g. the binding of a specific probe to a nucleic acid target molecule.

Certain embodiments of the invention provides for a solution to overcome the obstacles and obtain a SAW based method to analyse target molecule interactions which themselves are not directly detectable by SAW technology. Such method would be an alternative to methods known in the art such as e.g. those using fluorophore-quencer labels and where the attachment of fluorophore and/or quencher molecules does not provide the required signal sensitivity.

The microsensors disclosed herein include at least one surface acoustic wave sensor. A surface acoustic wave sensor includes a piezoelectric layer, or piezoelectric substrate, and input and output transducer(s). A surface acoustic wave is generated within the piezoelectric layer and is detected by interdigitated electrodes. As described in more detail below, binding events that alter the surface of the surface acoustic wave sensor can be detected as a change in a property of the propagating surface acoustic wave.

Acoustic wave devices are described by the mode of wave propagation through or on a piezoelectric substrate. Acoustic waves are distinguished primarily by their velocities and displacement directions. Many combinations are possible, depending on the material and boundary conditions. The interdigital transducer electrode (IDTE) of each sensor provides the electric field necessary to displace the substrate and thus form an acoustic wave. The wave propagates through the substrate, where it is converted back to an electric field at the IDTE at the opposing electrode. Transverse, or shear, waves have particle displacements that are normal to the direction of wave propagation and which can be polarized so that the particle displacements are either parallel to or normal to the sensing surface. Shear horizontal wave motion signifies transverse displacements polarized parallel to the sensing surface; shear vertical motion indicates transverse displacements normal to the surface.

"Surface acoustic wave sensor", or "surface acoustic wave device" as used herein means any device that operates substantially in the manner described above. In some embodiments, "surface acoustic wave sensor" refers to both surface transverse wave devices, where the surface displacement is perpendicular to the direction of propagation and parallel to the device surface, as well as surface acoustic wave sensors where at least a portion of the surface displacement is perpendicular to the device surface. While surface transverse wave devices generally have better sensitivity in a fluid, it has been shown that sufficient sensitivity may also be achieved when a portion of the surface displacement is perpendicular to the device surface.

The sensors are made by a photolithographic process. Manufacturing begins by carefully polishing and cleaning the piezoelectric substrate. Metal such as gold or aluminum is then deposited uniformly onto the substrate. The device is spin-coated with a photoresist and baked to harden it. It is then exposed to UV light through a mask with opaque areas corresponding to the areas to be metalised on the final device. The exposed areas undergo a chemical change that allows them to be removed with a developing solution. Finally, the remaining photoresist is removed. The pattern of metal remaining on the device is called an interdigital transducer (IDT) or interdigital electrodes (IDE). By changing the length, width, position, and thickness of the IDT, the performance of the sensor can be maximized.

Input and output transducers are preferably interdigitated transducers. Generally, there are two interdigital transducers. Each of the input and output transducers comprises two electrodes arranged in an interdigitated pattern. A voltage difference applied between the two electrodes of the input transducer results in the generation of a surface acoustic wave in the piezoelectric substrate. The electrodes generally may comprise any conductive material, such as e.g. aluminium or gold.

The electrode(s) may take any conventional form but are preferably photolithographically deposited on the surface as elongate regions of metallization transverse to the direction of propagation of a wave along the surface of the support. The elongate metallic regions preferably have a width and spacing of the same order of magnitude. The width is typically between 1 and 40 microns, preferably between 10 and 20 microns. In some embodiments, the width is greater than or equal to 100 nm, 200 nm, 300 nm, 400 nm, 500 nm, 600 nm, 700 nm, 800 nm, 900 nm, 1 micron, 2 microns, 3 microns, 4 microns, 5 microns, 7.5 microns, 10 microns, 15 microns, 20 microns, 25 microns, 30 microns, 35 microns, 40 microns, 45 microns, 50 microns, 60 microns, 70 microns, 80 microns or 90 microns.

In some embodiments, the space between the electrodes (channels) can be equal to or less than 100 microns, 90 microns, 80 microns, 70 microns, 60 microns, 50 microns, 45 microns, 40 microns, 35 microns, 30 microns, 25 microns, 20 microns, 15 microns, 10 microns, 7.5 microns, 5 microns, 4 microns, 3 microns, 2 microns 1 microns, 900 nm, 800 nm, 700 nm, 600 nm, 500 nm, 400 nm, 300 nm, 200 nm, 100 nm, or 75 nm. It should be noted that the spacing varies Inversely with the frequency of the device.

In some embodiments, the height of the electrodes is the same as the width of the electrodes. In other embodiments, the height of the electrodes is, for example, greater than or equal to 10 nm, 20 nm, 30 nm, 40 nm, 50 nm, 75 nm, 100 nm, 200 nm, 300 nm, 400 nm, 500 nm, 600 nm, 700 nm, 800 nm, or 900 nm.

In some embodiments, the depth of the space between the electrodes (channels) can be less than or equal to 1 micron, 900 nm, 800 nm, 700 nm, 600 nm, 500 nm, 400 nm, 300 nm, 200 nm, 100 nm, 75 nm, 50 nm, 40 nm, 30 nm, or 20 nm.

In some embodiments there is a single interdigital transducer. In this embodiment the single interdigital transducer, serves both as both an input and output transducer. In embodiments employing a single interdigital transducer which act both as input as well as output transducer, a reflector structure (resonator) is generally provided to generate one or more resonances within the SAW sensor. The reflector structure may, for example, be a thin film grating. The grating may comprise any conductive material such as e.g. aluminium or gold. The generated resonances can be detected, for example, by measuring the power dissipated at the single transducer. One or more binding events in the thin structure alter these resonances, allowing the binding events to be detected. As described below, other electronics and/or circuitry may similarly be utilized in an embodiment employing a SAW sensor having only one interdigital transducer.

In one embodiment the invention relates to a use of the reporter unit for detecting a nucleic acid target molecule, wherein the method further comprises a target molecule specific polymerase chain reaction during step a) and/or b).

The oligonucleotide probe may be used for monitoring a nucleic acid target molecule further employing nucleic acid amplification on a target sequence using a nucleic acid polymerase having 5' nuclease activity, a primer capable of hybridizing to the target sequence and an oligonucleotide probe according to the present invention which is capable of hybridizing to the target sequence 3' relative to the primer. The nucleic acid polymerase digests the oligonucleotide probe during amplification when it is hybridized to the target sequence, thereby liberating the component comprising the at least one substrate.

In one embodiment the invention relates to a use of the reporter unit for detecting a protein target molecule comprising the steps: a) Adding the reporter unit to the test sample potentially comprising the target molecule; b) Exposing the reporter unit/sample mixture of a) to the first enzyme, wherein said first enzyme has single stranded exonuclease activity; c) Exposing the mixture of b) to the second enzyme; and d) Analysing the polymerized structure on a SAW sensor.

In one embodiment the invention relates to a use of the reporter unit system for detecting a protein target molecule comprising the steps: a) Adding the test sample potentially comprising the target molecule to a target molecule specific immobilising agent; b) Adding the first enzyme linked to a target molecule specific probe to the mixture of a); c) Adding the pre-substrate comprising at least one component to the mixture of b); d) Adding the second enzyme to the mixture of c); and e) Analysing the polymerized structure on a SAW sensor.

In one embodiment the invention relates to a use of the reporter unit system for detecting a protein target molecule comprising the steps: a) Adding the test sample potentially comprising the target molecule to a target molecule specific immobilising agent; b) Adding the second enzyme linked to a target molecule specific probe to the mixture of a); c) Adding the substrate to the mixture of b); and d) Analysing the polymerized structure on a SAW sensor.

In one embodiment the invention relates to a use of the reporter unit or the reporter unit system for detecting a protein target molecule, wherein the first enzyme and/or the second enzyme is located on the SAW sensor area.

The enzymes such as e.g. PHA synthase, PHB synthase, nuclease etc. may be precipitated or immobilized on the surface of the SAW sensor. It could employ the whole area or only selected parts or elements of the surface of the SAW sensor such as e.g. the resonator, the interdigital transducer electrode (IDTE) area, the area between the IDTE, the area between the resonator and the IDTE, in the channels between the electrodes of the IDTE and/or the resonator, on top of the electrodes of the IDTE and/or the resonator. Alternatively, enzymes may be suspended in the solution applied to the SAW sensor.

EXAMPLE

This Invention is now illustrated by the following example that is not intended to be limiting in any way.

Example 1

Figure 1:
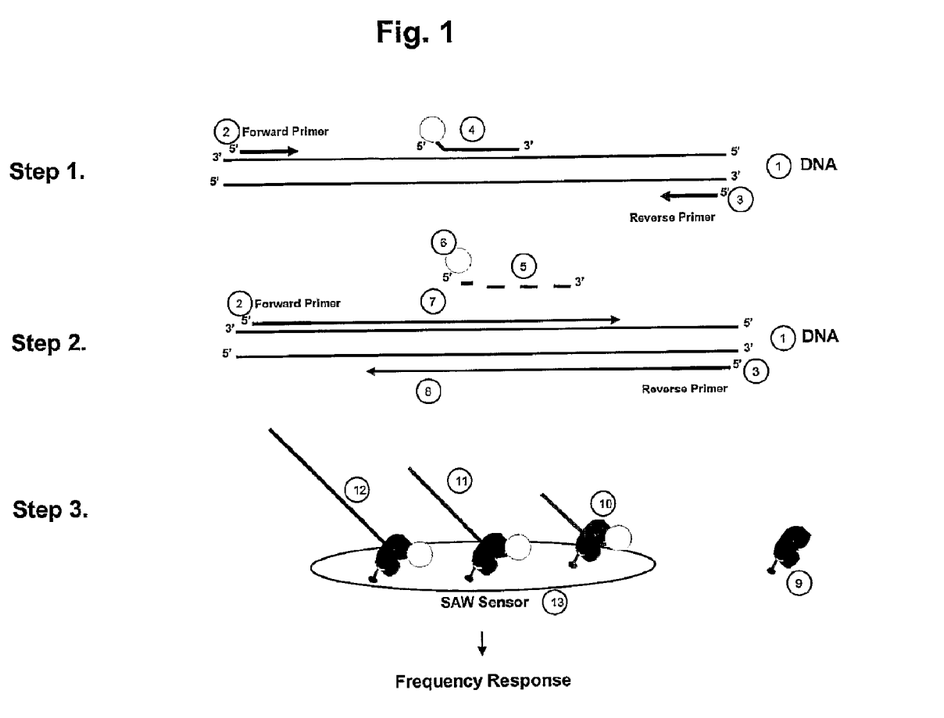
Figure 2:
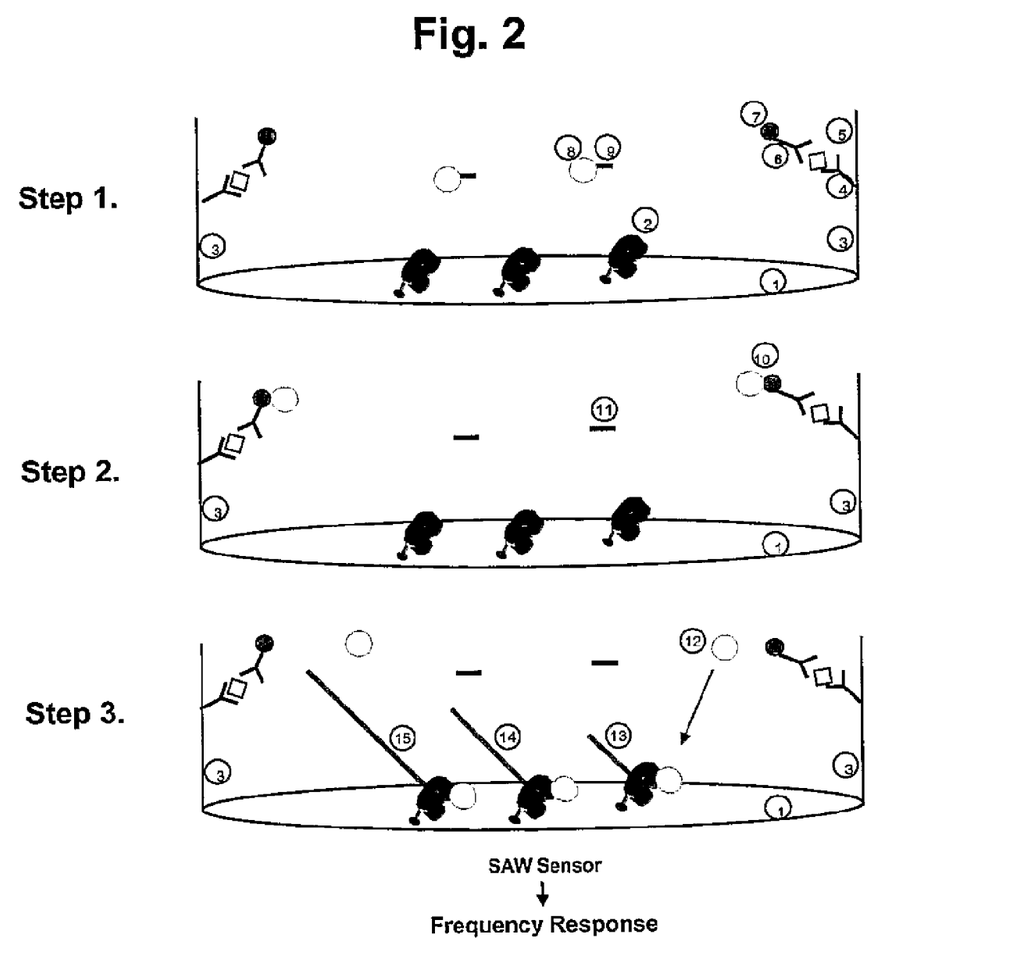
Figure 3:
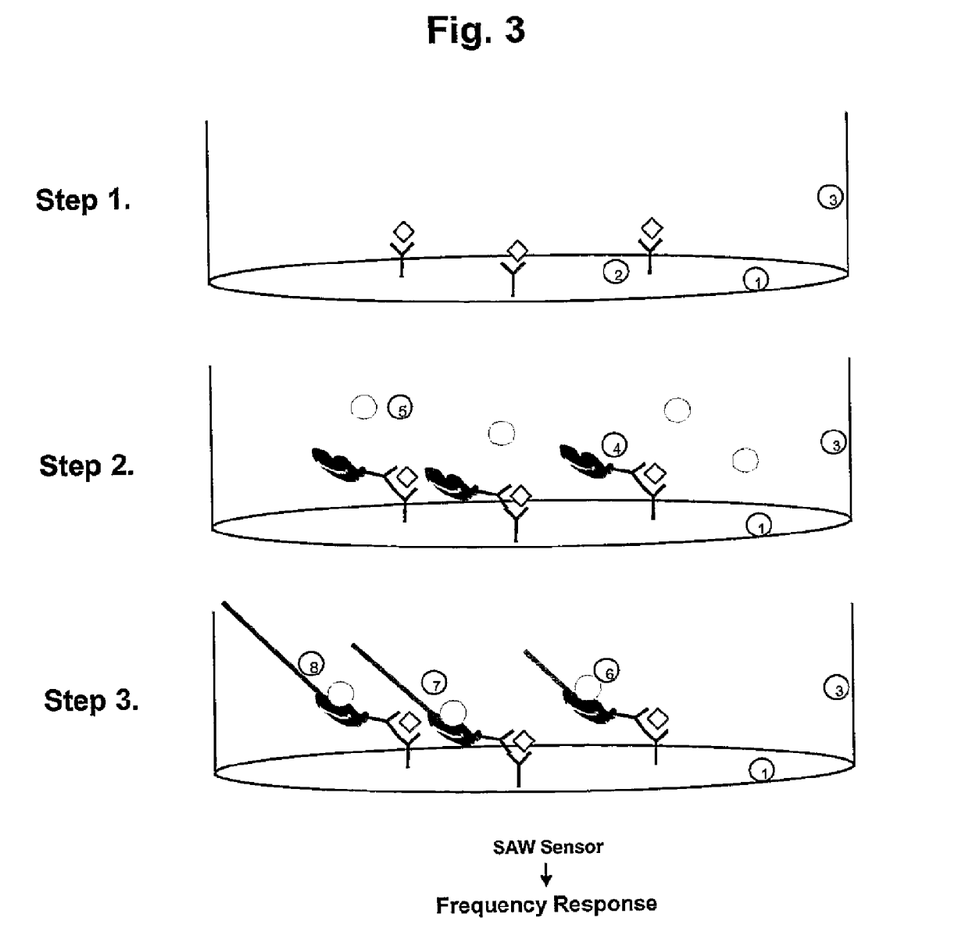
FIG. 3 illustrates a method for measuring a protein or peptide target molecule in a test sample on a SAW sensor surface (1) of a micro sensor. In step 1 the analyte (2) is immobilised to the SAW sensor surface (1) by a catching antibody. In step two the recognition unit (4) comprising the second enzyme attached to a target molecule specific probe (5) is added and allowed to bind to the analyte. The free substrate (5) is also added. In step three the polymerisation reaction results in a detectable polymeric structure (7, 8).
Figure 4:
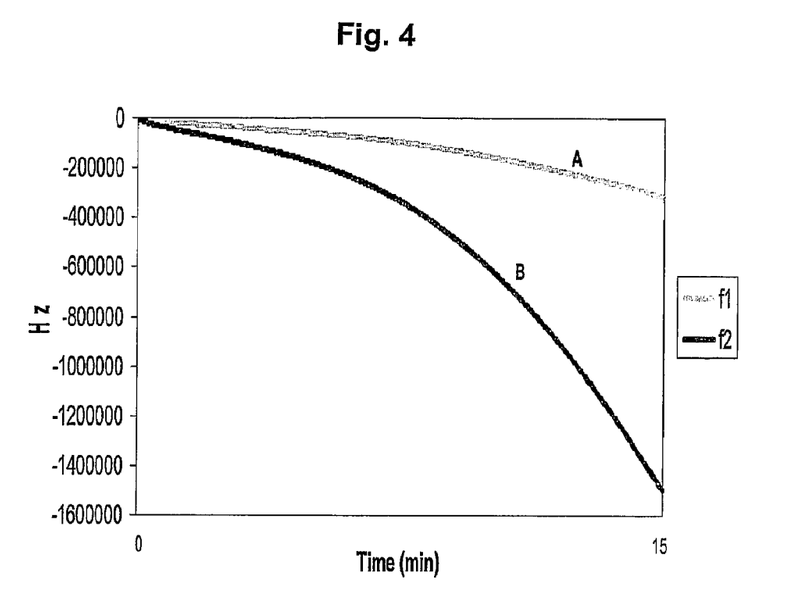
FIG. 4 illustrates the results of using a PHA synthase concentration of 10 ug/ml dry down on the sensor surface. Curve with the letter A displays the frequency in ppm having the substrate concentration of 1 mM. Curve with the letter B displays the frequency in ppm having the substrate concentration of 10 mM.
Figure 5:
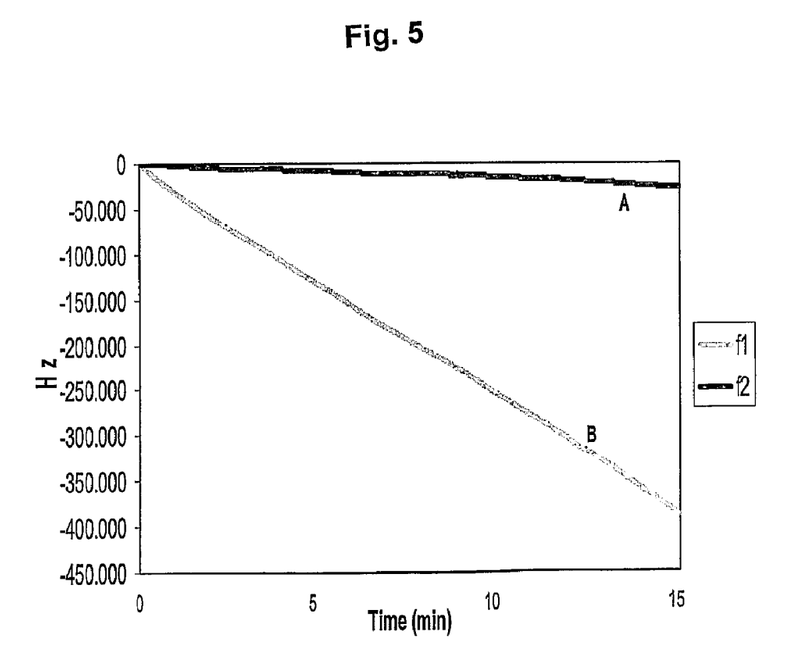
FIG. 5 illustrates the results of using a PHA Synthase concentration of 200 ug/ml dry down on the sensor surface. Curve with the letter A displays the frequency in ppm having the substrate concentration of 1 mM. Curve with the letter B displays the frequency in ppm having the substrate concentration of 10 mM.

Real Time Analysis of PHA Synthase Substrate Polymerization Detected by a Surface Acoustic Wave Sensor The PHA synthase (kindly provided by Professor Carl Batt, Cornell University, USA) was tested in two concentrations: 10 ug/ml and 200 ug/ml diluted in PBS buffer. The substrate, 3HB-CoA (purchased from Sigma Aldrich) was used in two concentrations: 1 mM and 10 mM.

The biosensor was a two port Shear horizontal surface acoustic wave (SH-SAW) resonator with two sensor elements named f1 and f2. The sensor area was 250 um×390 um and the surface was SiO2 (glass). The resonance frequency of the biosensor was 610 MHz. Ppm was calculated by dividing the measured frequency of each sensor element with 610 MHz. ppm is thus a measure for substrate polymerisation.

2 ul enzyme at a concentration of 10 ug/ml in experiment No. I, or 200 ug/ml in experiment No. II were applied to both sensor elements (f1 and f2). The enzyme was left on the biosensor elements for one hour at room temperature. At the beginning of each experiment a final concentration of 1 mM substrate was applied to sensor element 1 (f1) and 10 mM substrate was applied to sensor element 2 (f2). After 15 minutes ppm was calculated and the results are shown in Table I.

TABLE I

| | Ppm determined after 15 minutes | | |
|---|---|---|---|
| Biosensor Experiment No. | PHA synthase concentration (ug/ml) | f1 sensor element 1 mM substrate (ppm) | f2 sensor element 10 mM substrate (ppm) |
| I | 10 | −647 | −46 |
| II | 200 | −523 | −2494 |

Conclusions:

Polymerisation of the substrate (3HB-CoA) by PHA synthase was detectable by the Surface Acoustic Wave device. At low enzyme concentration (10 ug/ml) the application of a high substrate concentration (10 mM) did not increase the rate of substrate polymerization. Using a substrate concentration of 1 mM as compared to 10 mM resulted in a higher polymerization rate at low enzyme concentration (10 ug/ml). At high enzyme concentration, the high substrate concentrations (10 mM) generated a faster polymerization rate.

The invention claimed is:

1. A reporter unit for detecting a target molecule, said reporter unit comprising either:
   a. a coenzyme A (CoA) ester selected from the group consisting of (R)-3-Hydroxyacyl-CoA, (R)-3-Hydroxypropyryl-CoA, (R)-3-Hydroxybutyryl-CoA and Lactoyl-CoA, or (R)-3-Hydroxybutyryl-N-acetylcysteamin, where R is H, CH3, C2H5, C3H7, C4H9, C5H11, C6H13, C7H15, C8H17, C9H19, C10H21, C11H23, C12H25, C13H27 or C14H29 attached to a target molecule specific probe, or
   b. a target molecule specific probe attached to a first enzyme said first enzyme is capable of cleaving a pre-substrate comprising a coenzyme A (CoA) ester selected from the group consisting of (R)-3-Hydroxyacyl-CoA, (R)-3-Hydroxypropyryl-CoA, (R)-3-Hydroxybutyryl-CoA and Lactoyl-CoA, or (R)-3-Hydroxybutyryl-N-acetylcysteamin, where R is H, CH3, C2H5, C3H7, C4H9, C5H11, C6H13, C7H15, C8H17, C9H19, C10H21, C11H23, C12H25, C13H27 or C14H29, or
   c. a target molecule specific probe attached to a second enzyme, capable of employing a coenzyme A (CoA) ester selected from the group consisting of (R)-3-Hydroxyacyl-CoA, (R)-3-Hydroxypropyryl-CoA, (R)-3-Hydroxybutyryl-CoA and Lactoyl-CoA, or (R)-3-Hydroxybutyryl-N-acetylcysteamin, where R is H, CH3, C2H5, C3H7, C4H9, C5H11, C6H13, C7H15, C8H17, C9H19, C10H21, C11H23, C12H25, C13H27 or C14H29 as a substrate in a polymerization reaction to obtain a detectable structure.

2. The reporter unit or reporter unit system according to claim 1, wherein the coenzyme A (CoA) ester is attached to a label selected from the group consisting of dyes, fluorophores, quenchers, and radioactive substances.

3. The reporter unit or reporter unit system according to claim 1, wherein the probe comprises nucleic acids, nucleic acid derivatives, nucleic acid analogues, proteins, protein derivatives, protein analogues or any combination thereof.

4. The reporter unit or reporter unit system according to claim 3, wherein the probe comprises a blocking component at the 3'terminus whereby the probe is not able to extend the DNA strand from the 3'end.

5. The reporter unit or reporter unit system according to claim 1, wherein the first enzyme has double stranded exonuclease activity.

6. The reporter unit or reporter unit system according to claim 5, wherein the first enzyme is taq polymerase.

7. The reporter unit or reporter unit system according to claim 1, wherein the first enzyme has single stranded exonuclease activity.

8. The reporter unit or reporter unit system according to claim 7, wherein the first enzyme is Exo I.

9. The reporter unit or reporter unit system according to claim 1, wherein the first enzyme has 5' terminus exonuclease activity.

10. The reporter unit or reporter unit system according to claim 1, wherein the second enzyme is selected from the group consisting of polyhydroxyalkanoate (PHA) synthases and polyhydroxybutyrate (PHB) synthases.

11. The reporter unit or reporter unit system according to claim 10, wherein the polyhydroxyalkanoate (PHA) synthase is a class I, class II, class III or class IV synthase.

12. The reporter unit or reporter unit system according to claim 1, wherein the first enzyme and/or the second enzyme is thermostable.

13. Method for detecting a target molecule, the method comprising the steps of:
   a. adding a reporter unit according to claim 1, the reporter unit comprising a coenzyme A (CoA) ester selected from the group consisting of (R)-3-Hydroxyacyl-CoA, (R)-3-Hydroxypropyryl-CoA, (R)-3-Hydroxybutyryl-CoA and Lactoyl-CoA, or (R)-3-Hydroxybutyryl-N-acetylcysteamin, where R is H, CH3, C2H5, C3H7, C4H9, C5H11, C6H13, C7H15, C8H17, C9H19, C10H21, C11H23, C12H25, C13H27 or C14H29 attached to a target molecule specific probe to a test sample potentially comprising the target molecule;
   b. exposing the reporter unit/sample mixture of a) to a first enzyme capable of cleaving a pre-substrate comprising a coenzyme A (CoA) ester selected from the group consisting of (R)-3-Hydroxyacyl-CoA, (R)-3-Hydroxypropyryl-CoA, (R)-3-Hydroxybutyryl-CoA and Lactoyl-CoA, or (R)-3-Hydroxybutyryl-N-acetylcysteamin, where R is H, CH3, C2H5, C3H7, C4H9, C5H11, C6H13, C7H15, C8H17, C9H19, C10H21, C11H23, C12H25, C13H27 or C14H29;
   c. exposing the mixture of b) to a second enzyme capable of employing a coenzyme A (CoA) ester selected from the group consisting of (R)-3-Hydroxyacyl-CoA, (R)-3-Hydroxypropyryl-CoA, (R)-3-Hydroxybutyryl-CoA and Lactoyl-CoA, or (R)-3-Hydroxybutyryl-N-acetylcysteamin, where R is H, CH3, C2H5, C3H7, C4H9, C5H11, C6H13, C7H15, C8H17, C9H19, C10H21, C11H23, C12H25, C13H27 or C14H29 as a substrate in a polymerization reaction to obtain a detectable structure; and
   d. detecting the polymerized structure.

14. Method for detecting a nucleic acid target molecule the method comprising the steps of:
   a. adding a reporter unit according to claim 1, the reporter unit comprising a coenzyme A (CoA) ester selected from the group consisting of (R)-3-Hydroxyacyl-CoA, (R)-3-Hydroxypropyryl-CoA, (R)-3-Hydroxybutyryl-CoA and Lactoyl-CoA, or (R)-3-Hydroxybutyryl-N-acetylcysteamin, where R is H, CH3, C2H5, C3H7, C4H9, C5H11, C6H13, C7H15, C8H17, C9H19, C10H21, C11H23, C12H25, C13H27 or C14H29 attached to a target molecule specific probe to a test sample potentially comprising the target molecule;

b. exposing the reporter unit/sample mixture of a) to a first enzyme, wherein said first enzyme has double stranded exonuclease activity;

c. exposing the mixture of b) to the second enzyme capable of employing a coenzyme A (CoA) ester selected from the group consisting of (R)-3-Hydroxyacyl-CoA, (R)-3-Hydroxypropyryl-CoA, (R)-3-Hydroxybutyryl-CoA and Lactoyl-CoA, or (R)-3-Hydroxybutyryl-N-acetylcysteamin, where R is H, CH3, C2H5, C3H7, C4H9, C5H11, C6H13, C7H15, C8H17, C9H19, C10H21, C11H23, C12H25, C13H27 or C14H29 as a substrate in a polymerization reaction to obtain a detectable structure; and d. analysing the polymerized structure on a SAW sensor.

15. The method according to claim 3, wherein the method further comprises a target molecule specific polymerase chain reaction during step a) and/or b).

16. Method for detecting a protein target molecule, the method comprising the steps of:

a. adding the reporter unit according to claim 1, the reporter unit comprising a coenzyme A (CoA) ester selected from the group consisting of (R)-3-Hydroxyacyl-CoA, (R)-3-Hydroxypropyryl-CoA, (R)-3-Hydroxybutyryl-CoA and Lactoyl-CoA, or (R)-3-Hydroxybutyryl-N-acetylcysteamin, where R is H, CH3, C2H5, C3H7, C4H9, C5H11, C6H13, C7H15, C8H17, C9H19, C10H21, C11H23, C12H25, C13H27 or C14H29 attached to a target molecule specific probe, to the test sample potentially comprising the target molecule;

b. exposing the reporter unit/sample mixture of a) to a first enzyme, wherein said first enzyme has single stranded exonuclease activity;

c. exposing the mixture of b) to the second enzyme capable of employing a coenzyme A (CoA) ester selected from the group consisting of (R)-3-Hydroxyacyl-CoA, (R)-3-Hydroxypropyryl-CoA, (R)-3-Hydroxybutyryl-CoA and Lactoyl-CoA, or (R)-3-Hydroxybutyryl-N-acetylcysteamin, where R is H, CH3, C2H5, C3H7, C4H9, C5H11, C6H13, C7H15, C8H17, C9H19, C10H21, C11H23, C12H25, C13H27 or C14H29 as a substrate in a polymerization reaction to obtain a detectable structure; and d. analysing the polymerized structure on a SAW sensor.

17. Method for detecting a protein target molecule, the method comprising the steps of:

a. adding the test sample potentially comprising the target molecule to a target molecule specific immobilising agent;

b. adding a reporter unit system according to claim 1, the reporter unit comprising a target molecule specific probe attached to a first enzyme capable of cleaving a presubstrate comprising a coenzyme A (CoA) ester selected from the group consisting of (R)-3-Hydroxyacyl-CoA, (R)-3-Hydroxypropyryl-CoA, (R)-3-Hydroxybutyryl-CoA and Lactoyl-CoA, or (R)-3-Hydroxybutyryl-N-acetylcysteamin, where R is H, CH3, C2H5, C3H7, C4H9, C5H11, C6H13, C7H15, C8H17, C9H19, C10H21, C11H23, C12H25, C13H27 or C14H29, to the mixture of a);

c. adding a pre-substrate comprising a coenzyme A (CoA) ester selected from the group consisting of (R)-3-Hydroxyacyl-CoA, (R)-3-Hydroxypropyryl-CoA, (R)-3-Hydroxybutyryl-CoA and Lactoyl-CoA, or (R)-3-Hydroxybutyryl-N-acetylcysteamin, where R is H, CH3, C2H5, C3H7, C4H9, C5H11, C6H13, C7H15, C8H17, C9H19, C10H21, C11H23, C12H25, C13H27 or C14H29 to the mixture of b);

d. adding a second enzyme capable of employing a coenzyme A (CoA) ester selected from the group consisting of (R)-3-Hydroxyacyl-CoA, (R)-3-Hydroxypropyryl-CoA, (R)-3-Hydroxybutyryl-CoA and Lactoyl-CoA, or (R)-3-Hydroxybutyryl-N-acetylcysteamin, where R is H, CH3, C2H5, C3H7, C4H9, C5H11, C6H13, C7H15, C8H17, C9H19, C10H21, C11H23, C12H25, C13H27 or C14H29, as a substrate in a polymerization reaction to obtain a detectable structure to the mixture of c); and e. analysing the polymerized structure on a SAW sensor.

18. Use of, method for detecting a protein target molecule, the method comprising the steps of:

a. adding the test sample potentially comprising the target molecule to a target molecule specific immobilising agent;

b. adding a reporter unit system according to claim 1, the reporter unit comprising a target molecule specific probe attached to a second enzyme, capable of employing a coenzyme A (CoA) ester selected from the group consisting of (R)-3-Hydroxyacyl-CoA, (R)-3-Hydroxypropyryl-CoA, (R)-3-Hydroxybutyryl-CoA and Lactoyl-CoA, or (R)-3-Hydroxybutyryl-N-acetylcysteamin, where R is H, CH3, C2H5, C3H7, C4H9, C5H11, C6H13, C7H15, C8H17, C9H19, C10H21, C11H23, C12H25, C13H27 or C14H29, as a substrate in a polymerization reaction to obtain a detectable structure to the mixture of a);

c. adding the substrate to the mixture of b); and d. analysing the polymerized structure on a SAW sensor.

19. The method according to claim 3, wherein the first enzyme and/or the second enzyme is located on the SAW sensor area.

20. The use according to claim 13, wherein the first enzyme and/or the second enzyme is located on the SAW sensor area.

* * * * *